United States Patent
Wang et al.

(10) Patent No.: US 6,331,604 B1
(45) Date of Patent: Dec. 18, 2001

(54) GRAFTED RUBBER-LIKE SILICONE GEL WITH ENHANCED OIL COMPATIBILITY AND ITS SYNTHETIC PROCESS

(75) Inventors: James Wang, Stony Brook, NY (US); Thomas J. Hrubec, Elmwood Park, NJ (US)

(73) Assignee: Grant Industries, Inc., Elmwood Park, NJ (US)

( * ) Notice: Subject to any disclaimer, the term of this patent is extended or adjusted under 35 U.S.C. 154(b) by 0 days.

(21) Appl. No.: 09/269,631

(22) PCT Filed: Oct. 29, 1997

(86) PCT No.: PCT/US97/19715

§ 371 Date: Mar. 31, 1999

§ 102(e) Date: Mar. 31, 1999

(87) PCT Pub. No.: WO98/18849

PCT Pub. Date: May 7, 1998

Related U.S. Application Data

(60) Provisional application No. 60/029,774, filed on Oct. 29, 1996.

(51) Int. Cl.[7] .................................................. C08G 77/14
(52) U.S. Cl. .............................. 528/29; 528/31; 424/401; 524/731; 524/268
(58) Field of Search ........................ 528/29, 31; 424/401; 524/268, 731

(56) References Cited

U.S. PATENT DOCUMENTS

| | | | | |
|---|---|---|---|---|
| 4,426,480 | * | 1/1984 | Petty ...................................... | 524/445 |
| 4,532,132 | * | 7/1985 | Keil ........................................ | 514/772 |
| 4,732,929 | * | 3/1988 | Chang et al. ......................... | 524/541 |
| 4,990,556 | * | 2/1991 | Shimizu et al. ...................... | 524/475 |
| 5,310,842 | * | 5/1994 | Ichinohe et al. ...................... | 528/12 |
| 5,482,703 | * | 1/1996 | Pings ................................ | 424/70.12 |
| 5,665,804 | * | 9/1997 | Hill et al. .............................. | 524/268 |

* cited by examiner

Primary Examiner—Margaret G. Moore
(74) Attorney, Agent, or Firm—Woodbridge & Associates, P.C.; Stuart H. Nissim; Richard C. Woodbridge

(57) ABSTRACT

Fatty alcohol or aliphatic glycol-grafted rubber-like silicone gels with enhanced oil compatibility are synthesized by 1) reacting a fatty alcohol or a aliphatic glycol with methylhydrodimethylsiloxane copolymer in the presence of a platinum catalyst in a reaction medium of a silicone fluid or a cosmetic oil or a mixture thereof, and 2) further reacting the mixture with a vinyl-functional siloxane polymer. The resulting compounds may be used as gelling agents for hydrocarbon oils, vegetable oils and silicone oils. The efficient synthetic process approaches a 100% yield.

15 Claims, No Drawings

GRAFTED RUBBER-LIKE SILICONE GEL WITH ENHANCED OIL COMPATIBILITY AND ITS SYNTHETIC PROCESS

This application claim benefit to provisional application No. 60/029,774 Oct. 29,1996.

FIELD OF THE INVENTION

The present invention relates to silicone compositions, more particularly to a fatty alcohol- or aliphatic diol-grafted rubber-like silicone gel compositions and to a process for preparing them. The resulting compositions can be used as gelling agents for oils, including hydrocarbon oils, vegetable oils, and silicone oils. The process provides a simple and efficient method to prepare such compounds exhibiting high yield, high purity, and low cost.

BACKGROUND OF THE INVENTION

Oil gels are often desirable application vehicles for personal care products and cosmetic make-ups because they can provide a thin, water resistant, substantive film on skin. They are usually stable over time and convenient to apply. Some oily compounds exist in paste form at room temperature, such as Vaseline and lanolin, and may be directly utilized as an application vehicle. Others exist in liquid form, such as jojoba oil and bois oil, and may need to be converted to a gel form for use in a formulation. Various organic waxes, organic resins, and polymers have been employed as potential gelling agents for an oil medium. The resulting oil gels are generally very oily and particularly sticky if a polymer is utilized as the gelling agent.

Silicone polymers, particularly volatile silicones and low molecular weight silicones having a viscosity of below 50 cPs, have been used in an attempt to reduce the sticky feel and improve the extendibility but, they cannot reduce the oily feel and appearance on skin. Such an oily cosmetic composition is disclosed in U.S. Pat. No. 5,266.321, issued to Shukuzaki et al. Shukuzaki et al., disclose an oily make-up composition comprising an oil base, a silicone gel composition, and a cosmetic powder material. The silicone gel composition renders the make-up formulation less sticky and less oily, and provides a fresh, smooth feeling to the skin. The silicone gel composition disclosed therein consists essentially of a partially cross-linked organo polysiloxane and a low viscosity silicone oil. The silicone gel composition disclosed by Shakuzaki et al., however, is not quite compatible with most cosmetic oils. Its viscosity breaks down very sharply with an increased amount of a cosmetic oil, and thus it cannot be used as an efficient gelling agent. It may result in oil bleeding or phase split if incorporated in a cosmetic formulation.

In contrast to the art, the rubber-like silicone gel in the present invention comprises a fatty alcohol or aliphatic diol-grafted silicone network, as opposed to a pure silicone network, The compositions of the present invention demonstrate a sufficient compatibility with respect to the targeted cosmetic oils by maximizing the content of the fatty alcohol radical or aliphatic diol radical while preserving the desirable silicone characteristic.

The use of a silicone oil or a cosmetic oil or a mixture thereof, as opposed to a low viscosity silicone oil, also contributes to the beneficial characteristics of the compositions of the present invention.

The use of $H_2PtCl_6.6H_2O$, as opposed to organic metal salts such as tin octoate as a catalyst taught in the art, for the reaction between a fatty alcohol or $C_5$–$C_{22}$ aliphatic glycol and a methylhydrosiloxane polymer makes the process simpler and more efficient in terms of the yield, purity and cost.

SUMMARY OF TIE INVENTION

The present invention relates to a fatty alcohol- or a aliphatic diol-grafted rubber-like silicone gel which comprises a cross-linked fatty alcohol or aliphatic diol-grafted silicone network and a silicone fluid or a cosmetic oil or a mixture thereo, having a good compatibility with cosmetic oils and silicone oils and can be used as a gelling agent for these oils. The oil gels made by using the rubber-like silicone gel as a gelling agent provide a smooth, non-tacky, non-oily feel and can be utilized as an ideal cosmetic application vehicle.

The invention further relates to a method for preparing the said rubber-like silicone gel. This method involves a two step process: (1) reacting a fatty alcohol or aliphatic diol with a methylhydrodimethylsiloxane copolymer in the presence of an $H_2PtCl_6.6H_2O$ catalyst in a reaction medium of silicone oil or cosmetic oil or a mixture thereof and (2) further reacting the intermediate product mixture with vinyl silicone.

As the fatty alcohol radicals or aliphatic diol radicals are of high compatibility with most cosmetic oils, the cross-linked silicone network with these radicals chemically bonding on it has an increasingly higher compatibility with cosmetic oils than it would otherwise, and thus is capable of absorbing a considerable amount of those oils. The higher the level of the grafted radicals in the cross-linked silicone, the better the compatibility of the rubber-like silicone gel with those oils. The favored silicone characteristic will fade with increasing levels of radicals, therefore; the ratio of fatty alcohol radicals or aliphatic diol radicals to the silicone backbone should be balanced out according to the formulation requirement. A satisfactory result can be achieved when the level of fatty alcohol radicals or aliphatic diol radicals is about 3%–35%,.preferably 10–20%, by weight relative to the silicone backbone. The level of fatty alcohol or aliphatic diol radicals in the cross-linked silicone network can be easily varied in accordance with the synthesis of the present invention. This process provides a simple and efficient method for preparing a fatty alcohol- or aliphatic diol-grafted rubber-like silicone gel in terms of yield, purity and cost.

The level of radicals grafted on the crosslinked silicone can be controlled in the first step reaction of the present invention by changing the ratio of the fatty alcohol or aliphatic diol to the reactive silicone on the copolymer. The ratio is about 1:9 to 2:8 for an optimum balance between the oil compatibility and silicone characteristics. The oil compatibility also depends strongly upon the type of fatty alcohols or aliphatic diols used.

The process of the present invention is not limited to making silicone gel. This process may be easily modified to prepare fatty alcohol- or aliphatic diol-grafted silicone oils within the principle scope of the present invention.

The rubber-like silicone gel can then be mixed with a cosmetic oil, a silicone oil, or a mixture thereof. After the silicone gel swells up with the oil, the resulting product is ground to fine particles forming an oil gel useful in cosmetic and personal care products.

DETAILED DESCRIPTION OF THE INVENTION

A fatty alcohol- or aliphatic diol-grafted rubber-like silicone gel of this invention comprises a fatty alcohol- or aliphatic diol-grafted silicone network polymer; and, a silicone oil or a cosmetic oil or a mixture thereof This rubber-like silicone gel can be used as a gelling agent which will absorb up to about 400% of silicone oils or cosmetic oils relative to its own weight. The fully swelled granules of the said rubber-like silicone gel can be ground to a very smooth viscous gel form using, for example, a mixer of high shear rates or a three-roll mill. The resulting oil gel is an ideal cosmetic application vehicle that provides a fresh, smooth, non-tacky, non-oily feel on the skin.

The structure of the rubber-like silicone gel is characterized by a three-dimensional network of the repeat unit of Si—O backbone and two covalent organic radicals on each Si atom. The organic radicals include hydrogen atom, $C_1$–$C_3$ alkyl group, phenyl group or the like, reacted fatty alcohol radical, i.e., alkoxy group, and reacted $C_5$–$C_{22}$ diol radical, i.e., alkoxylol group. A typical chemical formula for the silicone network can be mainly described as containing a mixture of the following units:

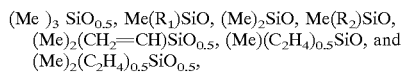

wherein $R_1$ is a hydrogen atom or vinyl group and $R_2$ is a $C_5$–$C_{22}$ alkoxy group or a $C_5$–$C_{22}$ alkoxylol group.

The ratio of the unit $Me(R_2)SiO$ to the rest of the units, by weight, can be from about 1:2 to about 1:30, preferably from about 1:3 to about 1:9. This ratio is related to the compatibility of the rubber-like silicone gel with the targeted silicone and cosmetic oils. At the low end, the silicone gel tends to show typical silicone properties, but a poor compatibility with cosmetic oils, whereas at the high end, it shows an increasing compatibility with cosmetic oils, but less silicone characters.

The crosslinking density of the rubber-like silicone gel is an important structural parameter that contributes to determining the end-use properties, such as oil absorption and smoothness of the resulting oil gel. Excessive crosslinking can cause the silicone rubber to become so hard that it cannot swell sufficiently in an oil to form a smooth gel. Insufficient crosslinking of the silicone network structure can cause the silicone rubber to be a loose network structure demonstrating insufficient absorption of oils.

The concentration of the silicone network, i.e., the solid content, affects substantially the gelation capacity. While a higher concentration of silicone network usually gives a higher gelation capacity, it may lead to a hard rubber and the oil gel made by using it may feel bumpy and grainy and therefore undesirable for use in cosmetic compositions. High concentration often leads to a more incomplete crosslinking due to a premature set-up of the system and thus the rubber-like gel has a lower gelation capacity in terms of the unit mass of the network. In practice, the silicone network concentration can be about 10–30% by weight, preferably 15–20% by weight.

The oils in the rubber-like silicone gel can be a silicone fluid or a cosmetic oil or a mixture thereof The silicone oils can be selected from the group of its kind such as cyclomethicone and dimethicone. The silicone oil preferably has a viscosity of up to 10,000 cPs, more preferably up to 1,000 cPs. The term "cosmetic oils" as used herein refers to any material which is substantially insoluble in water and acceptable for use in cosmetics or personal care products. Suitable cosmetic oils include, but are not limited to, hydrocarbon oils such as mineral oil, hydrogenated polyisobutene, isoparaffin oil and petrolatum; fatty alcohols such as octyldodecanol; vegetable oils such as coconut oil; aliphatic diols; esters such as $C_{12}$–$C_{15}$ alkyl benzoate; diesters such as propylene dipelarganate; triesters such as glyceryl trioctanoate; and the like. The cosmetic oils preferably have a viscosity of up to 10,000 cPs, more preferably up to 1,000 cPs.

The rubber-like silicone gel described above is prepared in a two-step process. In the first step, a fatty alcohol or diol is directly reacted with a methylhydrodimethyl siloxane copolymer in the presence of a catalyst of 2.0 wt % $H_2PtCl_6.6H_2O$ in isopropanol in a reaction medium of a silicone fluid or a cosmetic oil or a mixture thereof. The methylhydrodimethyl polysiloxane is selected such that the molecular weight range is about 700–10,000, preferably 2,000–9,000, and the number of Si—H units per molecular can be 4–35 preferably 15–25. The reaction takes place between the hydroxy group of the fatty alcohol or diol and the reactive Si—H group on the siloxane copolymer. This results in a linkage of Si—OR with the evolution of $H_2$, where OR is an alkoxy group from the fatty alcohol. Where a diol is used, the linkage of Si—OROH is obtained, where OROH is an alkoxylol group. The product from this step is a highly branched reactive silicone containing long branched chains of alkoxy radicals or alkoxy alkylol radicals. A significant quantity of reactive group Si—H in the product remains unreacted for a crosslinking reaction with a vinyl-silicone. A sufficient amount of Si—H unit is preserved for the crosslinking reaction by selecting the initial molar ratio of Si—H to fatty alcohol/diol radicals at a level such that at least three Si—H units remain in each molecule after reacting with the fatty alcohol/diol.

It is known that Si—H group can react with HOR in the presence of tin octoate, or zinc octoate or similar metal salt catalysts with the evolution of hydrogen, however; the reaction rate is extremely slow and inefficient requiring a time period of days or even weeks to complete the reaction. Therefore, it is not a practical approach for preparing such products. The inventor's of the present invention discovered that chloroplatinic acid $H_2PtCl_6.6H_2O$ dissolved in isopropanol at 2% by weight ( Speier's catalyst), can be used as a very effective catalyst for this reaction. Only a very small quantity is necessary, approximately, 5–20 ppm relative to the reactive Si—H groups. It requires only about 2 hours, at about $120$–$130°$ C., for the reaction between methylhydro polysiloxane and fatty alcohol or diol to be completed. The reaction is found very clean as no unreacted fatty alcohol can be detected on a high performance liquid chromatography (HPLC).

In the second step, the product from the first step is further reacted with a vinylsilicone, such as divinylsilicone or multivinyl silicone, to construct a three-dimensional network. The vinylsilicone is selected such that the molecular weight can be 700–15,000, preferably 2,000–9,000 and the average number of vinyl units per molecule can be 2–20, preferably 2–10. The reaction in this step occurs mainly between the unreacted Si—H groups remaining after the first step and the vinyl group C═C of vinylsilicone. This second step is a hydrosilylation reaction and is catalyzed by using Speier's catalyst. The Speier's catalyst which was added to the reaction mixture and utilized in the first step of the process is also utilized in this second step. As the reactants are all multifunctional, a crosslinking reaction takes place between reactive silicones with the viscosity of the reaction mixture developing rapidly and resulting in a rubber-like silicone gel. Additional polysiloxane can be added at this step to adjust the ratio of S—H reactive groups and thus control the crosslinking density.

The properties of the rubber-like silicone gel are mainly controlled by five factors: the molar ratio of Si—H to Si(CH=CH$_2$), the reaction temperature, and the concentration, molecular weight and functionality of the reactive silicones used.

The molar ratio of Si—H to Si(CH=CH$_2$) plays two main roles in the reaction. First, it determines the reaction rate. Within the defined range, the higher the ratio, the faster the reaction goes. This also applies to the post-curing after the reaction mixture has gelled up. Second, this ratio determines the hardness of the final silicone rubber product. When the ratio is on the high side, the silicone rubber usually becomes relatively hard provided that the functionality of the methylhydrodimethyl siloxane copolymer is greater than that of vinylsilicone, although the reaction takes place in 1:1 stoichiometry. In practice, the molar ratio of Si—H to Si(CH=CH$_2$) can be about 2:1 to 10:1. The preferred ratio is 2:1 to 4:1.

The reaction temperature also effects the reaction rate. A higher temperature makes the reaction proceed faster and is also beneficial to post-curing which proceeds extremely slowly at low temperatures taking days or months to complete. In the first step, the temperature range can be about 110–150° C., preferably about 130–140° C. In the second step, the temperature range can be about 70–130° C., with a preferred range of about 110–120° C.

The major role of the concentration of the reactants, which is the solid content of the, rubber-like silicone gel, is to control the softness and the oil absorption capacity. It is essential that a large portion of inert oil be present in the reaction mixture to act as (1) a reaction medium and (2) a plastisizer for the silicone network rubber. When the solid content is low, the silicone network rubber is generally too soft and too wet to absorb a significantly large volume of oil. When the solid content is high, the silicone rubber is often too hard and too dry to swell in an oil. The concentration of the reactants can be about 10–30% by weight. Preferably, the concentration of the reactants is about 13–20% by weight.

The molecular weight of the reactive silicones and their functionality are also important factors to be considered in the present invention. In the extreme end of high molecular weight of the reactive silicones, when the functionality is constant, the reaction gives a loose silicone rubber which tends to release the absorbed oil when being milled at high shear rates, while with low molecular weight reactive silicones, it is difficult to form an efficient silicone network rubber. When the functional group content is too high, the resulting silicone network rubber may be too hard to be useful for cosmetic or personal care compositions. In principle, the molecular weight and the functional group content can be in a wide range. The preferred molecular weight range for the reactive silicone is about 700–10,000, and the preferred functional group content is 1.5–25 mol %.

EXAMPLE 1

Stearyl Alcohol-Grafted Rubber-like Silicone Gel

To a 6 liter stainless steel reactor, add 181.5 g of methylhydrodimethyl siloxane copolymer having a molecular weight of about 4,000 and a molar content of methylhydro siloxane of 23.0%; 43.6 g of stearyl alcohol; 874.9 g of cyclic polydimethyl siloxane and 0.3 g of 2.0 wt % H$_2$PtCl$_6$.6H$_2$O in isopropanol. The reaction mixture is heated to about 130° C. and stirred for about 3 hours until the stearyl alcohol is completed grafted on the methylhydro dimethyl siloxane copolymer as determined by HPLC. Add 2467.0 g of cyclic dimethylsiloxane and 507.9 g of vinyl-terminal polysiloxane having a molecular weight of about 9,400. Stir the reaction mixture at 110° C. for about 30 minutes until the mixture becomes extremely viscous or a soft gel. Add 65.3 g of methylhydrodimethyl polysiloxane having a molecular weight of 2000 and a methylhydro siloxane molar content of 15% and mix slowly until a firm rubber-like gel sets up. Continue mixing the rubber-like gel at very low speed for about 2 hours at 100–110° C. until the post-curing is completed as determined such that the hardness of the rubber-like gel is no longer increased with time. This results in a granular product of 100% yield.

The rubber-like silicone gels of this invention can be used to make oil gels useful as application vehicles for cosmetic and personal care products.

EXAMPLE 2

Petrolatum Silicone Gel

Charge a 50 gallon stainless steel reactor with 10.66 kg of methylhydro dimethyl siloxane copolymer having a molecular weight of about 4,000 and a molar content of methylhydro siloxane of 23.0% ; 2.56 kg of stearyl alcohol; 51.385 kg of cyclic polydimethyl siloxane and 0.022 kg of 2 wt % H$_2$PtCl$_6$.6H$_2$O in isopropanol. Heat the reaction mixture to 130–140 and stir for about 3 hours until the stearyl alcohol is completely grafted on the methylhydro dimethyl siloxane copolymer as determined by HPLC. Add 79.165 kg of cyclic dimethylsiloxane and 29.831 kg of vinyl-terminal polysiloxane having a molecular weight of 9400. Stir thee reaction mixture at about 110° C. for about 30 minutes until the mixture becomes extremely viscous or a soft gel. Add 6.381 kg of methyl hydrodimethyl polysiloxane having a molecular weight of 2000 and a methylhydro molar content of 15% and mix slowly until a firm rubber-like gel sets up. Change the mixer to a low speed and continuously mix the rubber-like gel for about 2 hours at 100–110° C. until the post-curing is completed as determined such that the hardness of the rubber-like gel is no longer increased with time. This results in a granular product of rubber-like silicone gel with 100% yield.

Combine 30 parts by weight of the foregoing rubber-like silicone gel, 20 parts by weight of petrolatum and 50 parts by weight of cyclomethylsiloxane oil having a viscosity of about 0.65 cP. Grind this mixture using a high shear rate mixer until it becomes sufficiently smooth and free from granules. The viscosity is about 100,000 cPs.

EXAMPLE 3

Isoparaffin Silicone Gel

Prepare a rubber-like silicone gel according to Example 2. The isoparaffin silicone gel is prepared by premixing, by weight, 30 parts of the foregoing rubber-like silicone gel and 70 parts Of C$_{12}$-isoparaffin The mixture is then passed through a three-roll mill. The finished gel is clear and smooth and has a viscosity of about 70,000 cPs.

EXAMPLE 4

Bois Oil Silicone Gel

Prepare a rubberlike silicone gel according to Example 2. By weight, 35 parts of the rubberlike silicone gel, 21 parts of bois oil and 44 parts of a low viscosity silicone fluid are combined and mixed evenly. After the rubber is totally swelled, pass the mixture through a three-roll mill until a smpooth gel is produced. The resulting gel has a viscosity of about 70,000 cps.

These oil gels can be combined with commonly used inert and active materials such as protectives, adsorbents, pigments, demulcents, emnollients, astringents, antiperspirants, irritants, rubefacients, vesicants, cleansers, keratolytics, local anesthetics, and the like, to produce cosmetic and personal care products. Examples of such materials include, but are not limited to, aluminum magnesium silicate, benzocaine, black iron oxide, calcium carbonate, cellulose, coal tar, hydrocortisone, kaolin, magnesium carbonate, magnesium silicate, menthol, methylacrylate powder, mica, nylon powder, polyethylene powder, red iron oxide, silica, starch, styrene powder, talc, tar pigment, titanium dioxide, ultramarine blue, yellow iron oxide, zinc oxide, and the like.

The several examples set forth above are intended only to be illustrative. Other variations and modifications may be made in form and detail described herein without departing from the essential scope of the following claims.

We claim:

1. A cross-linked polydimethylsiloxane network characterized by the repeating units:

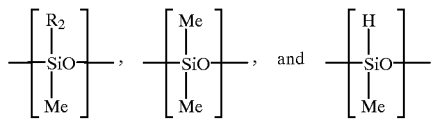

wherein $R_2$ is selected from the group consisting of $C_5$–$C_{22}$ alkoxy and $C_5$–$C_{22}$ alkoxylol and Me is methyl.

2. The cross-linked polydimethylsiloxane network of claim 1 further comprising one or more repeating units selected from the group consisting of $$(Me)_3SiO_{0.5}, (Me)_2(CH_2=CH)SiO_{0.5}, (Me)(CH_2CH_2)_{0.5}SiO, \text{ and } (Me)_2(CH_2CH_2)_{0.5}SiO_{0.5};$$

wherein Me is methyl.

3. The cross-linked polydimethylsiloxane network of claim 2 wherein said —Me($R_2$)SiO— repeating unit is present in a 1:2 to 1:30 ratio by weight to the combined weight of said —(Me$_2$)SiO—, —Me(H)SiO— and said one or more repeating units.

4. A grafted rubber-like silicone gel composition comprising:
   a grafted fatty alcohol or $C_5$–$C_{22}$ polydimethylsiloxane network; and,
   a cosmetic oil or a silicone oil or a mixture thereof.

5. A process for making a grafted silicone rubber composition, comprising the steps of:
   a) combing a fatty alcohol or fatty diol, methylhydrodimethyl polysiloxane, a silicone fluid or a mixture of a silicone oil and a cosmetic oil, and a chloroplatinic acid catalyst;
   b) heating the reaction mixture to 110–140° C. and stirring for about 3 hours until said fatty alcohol or fatty diol is completely grafted onto said methylhydrodimethyl polysiloxane as determined by HPLC;
   c) adding a divinyl- or multivinyl-silicone and mixing at 100–120° C. for about 0.5 hours until the reaction mixture becomes extremely viscous or a soft gel;
   d) mixing continuously at 100–110° C. for about 2 hours for post-curing.

6. The process of claim 5 wherein the ratio of fatty alcohols or diols to the reactive silicone is from 1:3 to 1:30 by weight.

7. The process of claim 5 wherein the overall molar ratio of Si—H of said polysiloxane remaining after step b) to Si(CH=CH2) of said vinylsilicone is 2:1 to 10-:1.

8. The process of claim 5 wherein the concentration of said silicone fluid or mixture of a silicone oil and a cosmetic oil is between 70–90% by weight based on the total combined weight of said fatty alcohol or fatty diol, methylhydrodimethyl polysiloxane, divinyl- or multivinyl-silicone, and silicone fluid or mixture of a silicone oil and a cosmetic oil.

9. The process of claim 5 wherein said methylhydrodimethyl polysiloxane has a molecular weight ranging from about 700 to about 10,000, and the number of Si—H units per molecular is 4 to 35.

10. The process of claim 5 wherein said vinylsilicone has a molecular weight ranging from about 700 to about 15,000 and having an average number of vinyl units per molecule of between 2 to 20.

11. The process of claim 5 wherein said silicone oil has a viscosity of up to 10,000 cPs at 25° C.

12. The process of claim 5 wherein said cosmetic oil is selected from the group consisting of hydrocarbon oils, fatty alcohols, aliphatic diols, esters and vegetable oils, having a viscosity of up to 10,000 cPs at 25° C.

13. A polydimethylsiloxane network made by:
   a) combining a fatty alcohol or fatty diol, methylhydrodimethyl polysiloxane, a silicone fluid or a mixture of a silicone oil and a cosmetic oil, and a chloroplatinic acid catalyst;
   b) heating and stirring to form a grafted polysiloxane; and
   c) cross-linking the grafted polysiloxane by adding a divinyl- or multivinyl-silicone and mixing with heat.

14. The polydimethylsiloxane network of claim 13 wherein, said polydimethylsiloxane network is characterized by the repeating unit:

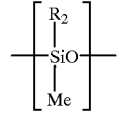

wherein $R_2$ is selected from the group consisting of $C_5$–$C_{22}$ alkoxy and $C_5$–$C_{22}$ alkoxylol; and Me is methyl.

15. A grafted rubber-like silicone gel composition comprising:
   a grafted polydimethylsiloxane network prepared by:
      combining a fatty alcohol or fatty diol, methylhydrodimethyl polysiloxane, a first silicone oil or a mixture of a first silicone oil and a first cosmetic oil, and a chloroplatinic acid catalyst;
      heating and stirring to form a grafted polysiloxane; and
      cross-linking the grafted polysiloxane by adding a divinyl- or multivinyl-silicone to and mixing with heat to produce a gel; and,
   a second cosmetic oil or a second silicone oil or a mixture thereof.

* * * * *